United States Patent
Levy et al.

(10) Patent No.: US 10,278,422 B2
(45) Date of Patent: May 7, 2019

(54) ELECTRONIC CIGARETTE WITH REDUCED ENERGY CONSUMPTION AND ENVIRONMENTAL IMPACT

(71) Applicant: Altria Israel LTD, Beit Shemesh (IL)

(72) Inventors: Dorron Levy, Givatayim (IL); Yaron Levy, Kfar Saba (IL); Robert Levitz, North Miami Beach, FL (US); David Cohen, Harei Yehuda (IL)

(73) Assignee: Altria Client Services LLC, Richmond, VA (US)

( * ) Notice: Subject to any disclaimer, the term of this patent is extended or adjusted under 35 U.S.C. 154(b) by 799 days.

(21) Appl. No.: 14/464,397

(22) Filed: Aug. 20, 2014

(65) Prior Publication Data

US 2015/0053220 A1    Feb. 26, 2015

Related U.S. Application Data

(66) Substitute for application No. 61/870,073, filed on Aug. 26, 2013.

(51) Int. Cl.
  *A24F 47/00*    (2006.01)
(52) U.S. Cl.
  CPC .................................. *A24F 47/008* (2013.01)
(58) Field of Classification Search
  CPC .......................... A61M 15/0021; A24F 47/008
  USPC .......................................................... 131/329
  See application file for complete search history.

(56) References Cited

U.S. PATENT DOCUMENTS

| | | | |
|---|---|---|---|
| 7,131,599 B2 * | 11/2006 | Katase | A61M 15/02 239/102.1 |
| 8,511,318 B2 * | 8/2013 | Hon | A24F 47/002 131/273 |
| 9,254,007 B2 * | 2/2016 | Liu | A24F 47/008 |
| 10,004,870 B2 * | 6/2018 | Yamada | A61M 15/06 |
| 2006/0196518 A1 * | 9/2006 | Hon | A24F 47/002 131/360 |
| 2006/0272659 A1 * | 12/2006 | Kobal | A24F 13/06 131/187 |

(Continued)

FOREIGN PATENT DOCUMENTS

DE         2653133 A1    5/1978
WO   WO-2011/117580     9/2011

(Continued)

OTHER PUBLICATIONS

Invitation to Pay Additional Fees dated May 6, 2015.

(Continued)

*Primary Examiner* — Eric Yaary
*Assistant Examiner* — Russell E Sparks
(74) *Attorney, Agent, or Firm* — Harness, Dickey & Pierce, P.L.C.

(57) ABSTRACT

A cartomizer of an electronic cigarette is configured to couple to a power source thereof that provides power for the electronic cigarette. The cartomizer comprises an insulated heating chamber that includes a controlled valve, a heating element, and an e-Liquid portion. The controlled valve can supply e-Liquid from the e-Liquid portion to the insulated heating chamber, wherein the e-Liquid is heated within the insulated heating chamber by the heating element to produce an aerosol. The insulated heating chamber reduces heat dissipation to the remainder of the cartomizer.

3 Claims, 3 Drawing Sheets

(56) References Cited

U.S. PATENT DOCUMENTS

| | | | | |
|---|---|---|---|---|
| 2007/0102013 | A1* | 5/2007 | Adams | A24F 47/008 |
| | | | | 131/273 |
| 2011/0005535 | A1* | 1/2011 | Xiu | A24F 47/008 |
| | | | | 131/273 |
| 2013/0061861 | A1* | 3/2013 | Hearn | A24F 47/006 |
| | | | | 131/329 |
| 2013/0192617 | A1 | 8/2013 | Thompson | |
| 2013/0199528 | A1* | 8/2013 | Goodman | F22B 1/282 |
| | | | | 128/203.26 |
| 2013/0284192 | A1* | 10/2013 | Peleg | A24F 47/002 |
| | | | | 131/329 |
| 2016/0021930 | A1* | 1/2016 | Minskoff | A61M 15/06 |
| | | | | 131/329 |

FOREIGN PATENT DOCUMENTS

| | | |
|---|---|---|
| WO | WO-2011117580 | 9/2011 |
| WO | WO-2012072264 A1 | 6/2012 |
| WO | WO-2013050934 A1 | 4/2013 |
| WO | WO-2013093470 A2 | 6/2013 |

OTHER PUBLICATIONS

International Search Report PCT/ISA/210 for International Application No. PCT/IB2014/002764 dated Oct. 15, 2015.
Written Opinion of the International Searching Authority PCT/ISA/237 for International Application No. PCT/IB2014/002764 dated Oct. 15, 2015.

* cited by examiner

ELECTRONIC CIGARETTE WITH REDUCED ENERGY CONSUMPTION AND ENVIRONMENTAL IMPACT

CROSS-REFERENCE TO RELATED APPLICATIONS

This application claims priority under 35 U.S.C. § 119(e) to U.S. provisional Application No. 61/870,073 filed Aug. 26, 2013, the disclosure of which is hereby incorporated herein by reference.

BACKGROUND

A traditional electronic cigarette ("e-cigarette" or "e-Cig") is a device that emulates tobacco cigarette smoking, by producing smoke replacement that may be similar in its physical sensation, general appearance, and sometimes flavor (i.e., with tobacco fragrance, menthol taste, added nicotine etc.). A battery portion of the e-Cig includes a controller and battery for powering the device and a cartomizer portion generates an aerosol mist (i.e. vapor) that is a replacement for cigarette smoke. In particular, the cartomizer may use heat (e.g. a heating element), ultrasonic energy, or other means to vaporize a liquid solution or "e-Liquid" (for example including propylene glycol, or glycerin, for example including taste and fragrance ingredients) into an aerosol mist. The component in the cartomizer portion that generates the aerosol mist may be referred to as an aerosol mist generator. The e-Cig may be powered by a power source, such as a battery which provides current for the heating. The power source may be difficult to regulate and result in a shorter life-span for the e-Cig by requiring re-charging.

The e-Liquid may be kept in a small container (sometimes called "cartomizer", which may be the approximate size of a regular cigarette's filter), and during the puff some of it is heated while being close to and around a heating coil (for example operated by a battery, and controlled via a control chip and a puff sensor). The heated e-Liquid loses its high viscosity, and then is prone to vaporization and some evaporation, generating the "smoke" to be inhaled by the user.

The vaporization may be enhanced by the usage of an e-Liquid-soaked wick inside a heating coil, wherein the small spaces between the wick fibers and small spaces inside the wick fibers enhance the breaking of the heated e-Liquid to small droplets generating the fog-like smoke. Some of the vaporized e-liquid may re-condensate to droplets, creating more fog-like smoke, due to the mix of the inhaled room-temperature air with the heated air and vapor inside the cartomizer. The fog-like smoke effect can also be enhanced by the high temperatures generated by the electrically-energized heated coil, combined with air flow (that reduces pressure around the wick due to the Bernoulli's principle, thus enhancing evaporation rate) which both enhance evaporation rate, and thereby load the air around the heating coil and wick with e-Liquid vapors. When the air round the heating coil and wick is saturated with e-Liquid vapors, and is hit by the room-temperature air flow sucked in by the user, some of its vapor may condensate into small air-borne droplets (similar to water fog in air) and add to the "smoke" generated by the e-Cig.

A unique problem that may arise due to the fog-like smoke effect mechanism of operation may include the depletion of high-boiling-temperature components in the vapors (low boiling temperature components boil first), wherein the high-boiling-temperature components may be lacking in the re-condensed droplets and fog. This may be of interest concerning e-Cigs with nicotine, wherein the nicotine has relatively high boiling points; the possibly re-condensed fog will be weak in nicotine, negating the effects expected by the user. Low nicotine absorption may be an issue with e-Cigs. The fact that the vaporized "smoke" can be generated from nicotine-depleted re-condensed vapor may at least partially explain it.

In some embodiments, the entire e-Liquid containing volume in the e-Cig, and its surrounding walls and other parts, are heated by the heating coil during the smoking puffs' duration. Eventually the entire e-Cig mouthpiece may feel warm in the hand and mouth of a user, and sometimes the e-Cig mouthpiece may even get overheated. Still, only the e-Liquid volume that is close to the heating coil and wick combination may generate most of the "smoke". Even the e-Liquid that is soaked in the wick, which may be heated by the heating coil, can be about twenty times or more in quantity than the e-Liquid that is eventually vaporized by the heating coil.

The growing popularity of e-Cigs emphasizes some of the challenges the industry faces, including the need for longer life-span, more efficient e-Cigs, and the environmental impact of used and discarded e-Cigs. There are several considerations to consider to overcome the challenges the industry faces, including: e-Cigs that are more energy-efficient, better e-Cig life span, reduced cost, ability to use smaller and lighter batteries, lighter e-Cigs (making the e-Cig more similar to regular cigarettes, which are light-weight), reduced waste, and possibly better control methods and user experience design.

SUMMARY

Disclosed herein is a cartomizer of an electronic cigarette wherein the cartomizer is configured to couple to a power source portion thereof that provides power for the electronic cigarette. The cartomizer comprises an insulated heating chamber that includes a controlled valve, a heating element, and an e-Liquid portion. The controlled valve can supply e-Liquid from the e-Liquid portion to the insulated heating chamber, wherein the e-Liquid is heated within the insulated heating chamber by the heating element to produce an aerosol. The insulated heating chamber reduces heat dissipation to the remainder of the cartomizer.

Also disclosed herein is an electronic cigarette which comprises an e-Liquid container with e-Liquid to be aerosolized, a controlled valve including a membrane with small passageways for reducing droplet size of an e-Liquid or vapor, and a spray mechanism for causing the e-Liquid to pass through the membrane.

Additionally disclosed herein is an electronic cigarette which comprises an e-Liquid container with e-Liquid to be aerosolized, and a rotation mechanism that is rotated by airflow through the electronic cigarette. The rotation causes a shearing force on the e-Liquid which results in an aerosolization of the e-Liquid.

BRIEF DESCRIPTION OF THE DRAWINGS

The system and method may be better understood with reference to the following drawings and description. Non-limiting and non-exhaustive embodiments are described with reference to the following drawings. The components in the drawings are not necessarily to scale, emphasis instead being placed upon illustrating the principles of embodiments

DETAILED DESCRIPTION

Figure 1:
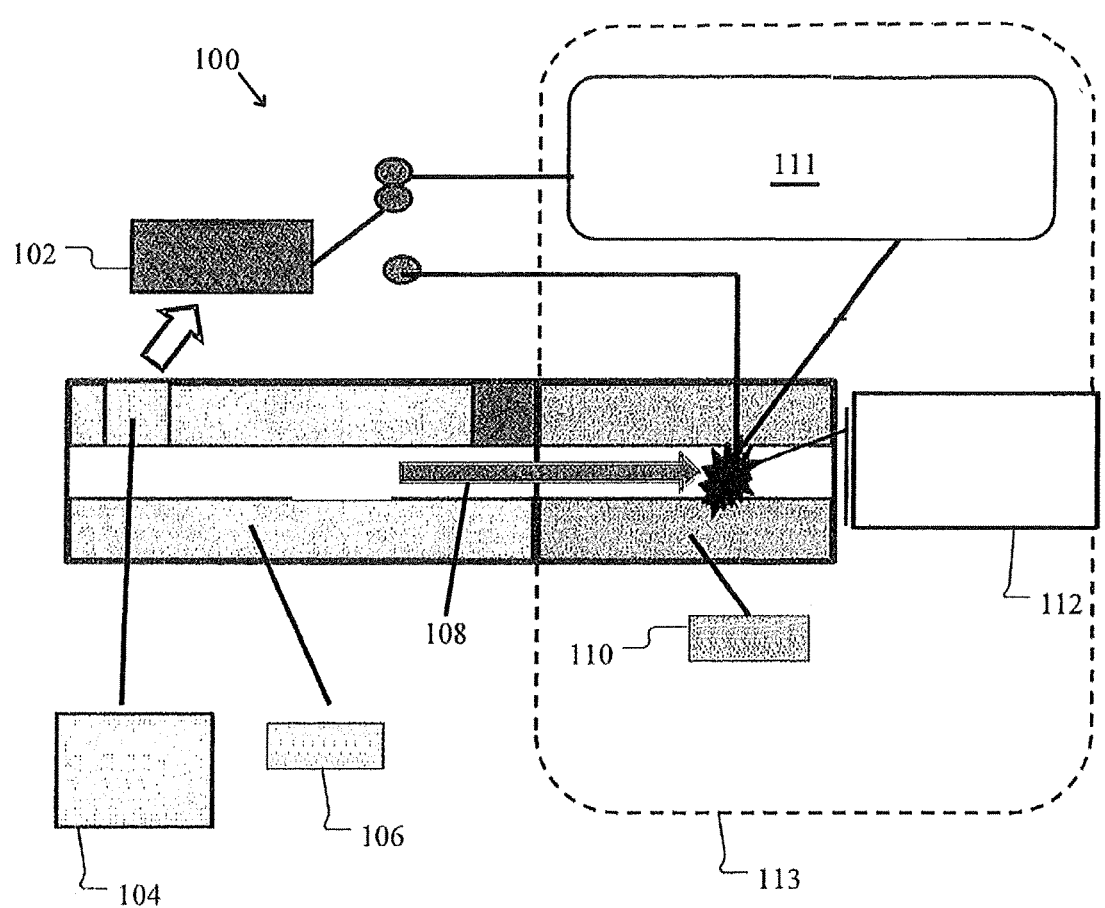
FIG. 1 is a diagram of a traditional electronic cigarette with a power source.

By way of introduction, a system and method may be described for an e-Cig which is more efficient and energy efficient. The e-Liquid that is aerosolized may be limited to extend the life of the e-Cig. The aerosolization process may be, generated through alternative sources other than a battery. In particular, the e-Cig may not require a battery or power source to generate aerosolization, which may be more energy efficient, environmentally friendly, and result in a longer life for the e-Cig.

Other systems, methods, features and advantages will be, or will become, apparent to one with skill in the art upon examination of the following figures and detailed description. It is intended that all such additional systems, methods, features and advantages be included within this description, be within the scope of embodiments disclosed herein, and be protected by the following claims. Nothing in this section should be taken as a limitation on those claims. Further aspects and advantages are discussed below.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

FIG. 1 is a diagram of an electronic cigarette with a power source 106. In traditional e-Cigs, the power source 106 was a battery. As further described below in FIG. 2, the e-Cig may be used without a battery. In particular, the power source 106 is through sources other than a battery.

The "smoke" produced by an e-Cig 100 is created by turning a liquid (e-Liquid 110) into mist and some vapor with an aerosol mist generator 112. The cartomizer 113 may include the aerosol mist generator 112 and the e-Liquid 110. The cartomizer 113 may also be referred to as a cartridge throughout this disclosure and may be disposable. The e-Liquid 110 may have a high viscosity at room temperature to enable longer shelf life and reduce leakages; however, this high viscosity may reduce the aerosolization rate. The e-Liquid 110 can be aerosolized via air flow 108, generated by the inhalation of the user (i.e. the smoker or consumer or vapor), which produces a pressure difference that removes e-Liquid droplets from the e-Liquid 110. In one embodiment, the e-Liquid 110 may be soaked in a wick (not shown). In order to reduce the e-Liquid viscosity, to a level enabling aerosolization, external heat may be applied through a heating element 111. The heating element 111 may be a coil in one embodiment that wraps around the wick in order to heat the e-Liquid on the wick. In this embodiment, local viscosity reduction via heating, while inhalation occurs, enables e-Liquid aerosolization in the inhalation-generated flow of air 108. The e-Liquid 110 may be heated via an electric current flowing through the heating element 111 and may then be vaporized and evaporated through the e-Cig 100 and may contain tastes and aromas that create a smoking sensation. A controller 102 may be activated due to air flow 108 (from the inhaled air) passing a puff sensor 104. The puff sensor 104 may be activated by a pressure drop across the puff sensor 104 and may directly switch the power source 106 power on, or be used as an input for the controller 102 that then switches the power source 106 current on. Although illustrated as separate from the e-Cig, the controller 102 may be a part of the e-Cig (e.g. along with the power source 106). The power source 106 may be a separate/removable assembly. The power source 106 may include one or more electronic chips controlling and communicating therefrom. The power source 106 may connect with the cartomizer 113, which can be replaced or changed (e.g. when a new/different e-Liquid 110 is desired).

Referring to FIG. 1, the e-Cig 100 may include two parts. The first part is often just referred to as the battery or battery portion (i.e. battery enclosure) and it includes the power source 106, the puff sensor 104 and the controller 102. The second part is the cartridge (i.e. cartomizer 113) that includes e-Liquid 110 and flavors that are required for "smoke" and flavor generation. The battery portion and the cartridge may be connected by metal connectors. The battery enclosure and the cartridge may be in fluid communication to enable a smoker to puff on a mouth end of the cartridge of the electronic cigarette and activate the puff sensor 104 inside the battery portion. This may trigger the controller 102 and cause the coil inside the cartridge to get hot, evaporate the e-Liquid that is in the cartridge and cause aerosolization of the e-Liquid (i.e. smoke or vapor).

Although not shown in FIG. 1, the e-Cig 100 may include connections (i.e. connectors or electrical connections) that are used for power delivery to the heating element 111 and for charging the power source 106.

Figure 2:
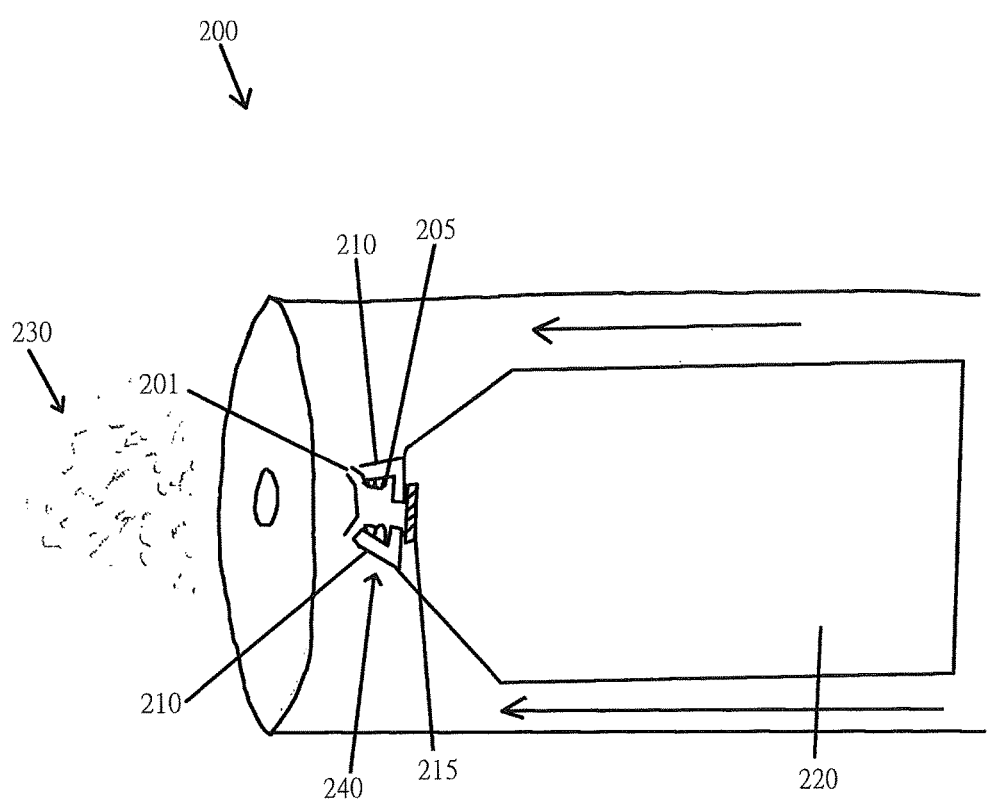
FIG. 2 is a diagram of an electronic cigarette with limited e-Liquid volume heated inside an insulated chamber.

FIG. 2 is a diagram of an electronic cigarette 200 with limited e-Liquid volume heating. In an embodiment, energy conserving considerations may limit the amount of the e-Liquid that is heated, to an amount closer to that which is converted into foggy e-Smoke 230 during a single puff. By constructing an insulated heating chamber 240 with at least some insulating walls 210, aerosolization holes 201, and a heating element 205, heat dissipation may be reduced, and therefore, the amount of e-Liquid that is heated can be reduced.

In prior e-Cig designs, a typical mechanism includes a wick that is surrounded by a heating coil. While the prior embodiments of e-Cig designs may vaporize approximately 4 mg of e-Liquid during a puff, the heating coil heats the entire wick during the puff wherein the heating coil may hold 100 mg or more of e-Liquid. The heating element 205, as shown in FIG. 2, may be different than a customary heating coil, common in e-Cigs, and rather be part of the inside of a wall of the insulated heating chamber 240. Accordingly, heating of the rest of the volume of e-Liquid disposed on a wick as mentioned above will be minimized, and overall energy consumption will be reduced, leading to enhanced power source lifespan.

Other advantages may include more accurate temperature control of the heated volume of e-Liquid due to a smaller mass of e-Liquid to be heated during a puff (and mass cooled between puffs) which reduces the thermal inertia of the mass of e-Liquid and consequently the properties of the e-Smoke 230 produced. This may result in better e-Liquid preservation, including avoidance of burning or charring taste, possibly related to overheating (when a larger than necessary e-Liquid volume is heated). When the heated e-Liquid volume is restricted to a relatively small quantity, with the heating done in a restricted volume of the insulated heating chamber 240 with thermally-insulated walls 210, the e-Liquid may be heated to the exact temperature required with no overheating.

For example, if a prior e-Cig, as described above, is calibrated for some overheating to overcome heat leakage to the rest of the e-Liquid in the cartomizer and to the cartomizer body, charring and burning may occur in hot spots of the coil, for example where the coil touches the wick, or for example, when the e-Liquid is about to be depleted and there is not enough of the e-Liquid, leading to increased temperature (same heating energy applied to less e-Liquid) and charring. With limited volume, overheating is not necessary, and may be for example limited to lower maximal temperature by a control chip, avoiding charring risks.

Other advantages of the insulated heating chamber 240 can be better preservation of the remainder e-Liquid in an e-Liquid container 220, especially properties of the e-Liquid which are more sensitive-to-heat traits such as fragrance, during the smoking session and between sessions (this may be due to the fact that the average temperature of the e-Liquid will be lower if it is not heated; it is reasonable to assume that every additional 10 degrees centigrade average temperature may reduce life span of the e-Liquid by a factor of 2; and manual or automated means can accurately manage puff volume, thus satisfying changing need of smokers (for the same smoker, or for different smokers with various needs). For example, the volume of the insulated heating chamber 240 may be changed, for example by mechanically changing its volume via inserting or removing solid material pieces, or by moving or rearranging the walls of the insulated heating chamber 240.

One embodiment, as disclosed herein may utilize e-Liquid aerosolization while eliminating the need for a battery, and consequently the use of heat, in producing the e-Smoke. Generating e-Smoke without heat may be done according to several different embodiments. While spray generation mechanisms that utilize, for example, manual operation such as perfume aerosolizers, or for example pressurized cans, do not utilize heat to generate spray, their direct utilization in e-Cigs may be limited. The spray may consist of relatively large droplets, with limited ability to reach the upper respiratory system and deliver the required nicotine and fragrance to the user. In an embodiment, in order to achieve smaller droplets, the controlled valve 215 which the e-Liquid in this embodiment can pass through for example by direct pressure or using the Bernoulli principle, through smaller holes thereof, for example through a punctured membrane, a cloth, a sponge, or any other related exemplary means. The size of droplets may be influenced by the mean structure (as shown empirically), for example, a cloth with various fiber count, using one or more layers of cloth, tension applied on the cloth etc. these means of control may be applied manually or automatically, to satisfy the needs of various smokers or the same smokers at differs occasions, for example through the control of the "smoke" droplet size. The e-Liquid may be changed and adapted to have the proper viscosity and other properties required for this embodiment.

Another energy and environmental improvement may be achieved by reducing the e-Liquid viscosity by means other than heat. For example, e-Liquid aerosolization may be induced by the puff airflow itself, flowing near an e-Liquid-containing small space and employing the Venturi effect. The following are potential examples for this form of aerosolization, but are merely exemplary. There may be other mechanisms for aerosolizing an e-Liquid using the puff airflow.

In one embodiment, an e-Cig 200 that does not require heat for viscosity management may use an e-Liquid with low viscosity. Using low viscosity e-Liquid may render the e-Cig prone to dry-out and leaks; however, this may be avoided with a possible embodiment of a sealed e-Liquid container 220, and the controlled valve 215 (i.e. a portioning mechanism) similar to what was described above with respect to FIG. 2. Some possible controlled valve 215 mechanisms that can drive the e-Liquid out of the sealed e-Liquid container 220 and into the smaller container wherein the e-Liquid will be aerosolized during the puff may include a pressurized container and valve, sponge mechanisms, mechanical squeezing (manual or electrical) mechanisms, a spray mechanism and more. A possible lower viscosity e-Liquid may consist of water, combined with taste, fragrance and other materials as needed. A water-based e-Liquid may be safer and easier to use. In an embodiment, the controlled valve 315 can include a spray mechanism and a membrane with small passageways wherein the spray mechanism is operable to pass e-Liquid through the membrane and the small passageways of the membrane are operable to reduce droplet size of the e-Liquid or vapor formed from the e-Liquid. In an embodiment the small passageways form aerosolization holes.

Figure 3:
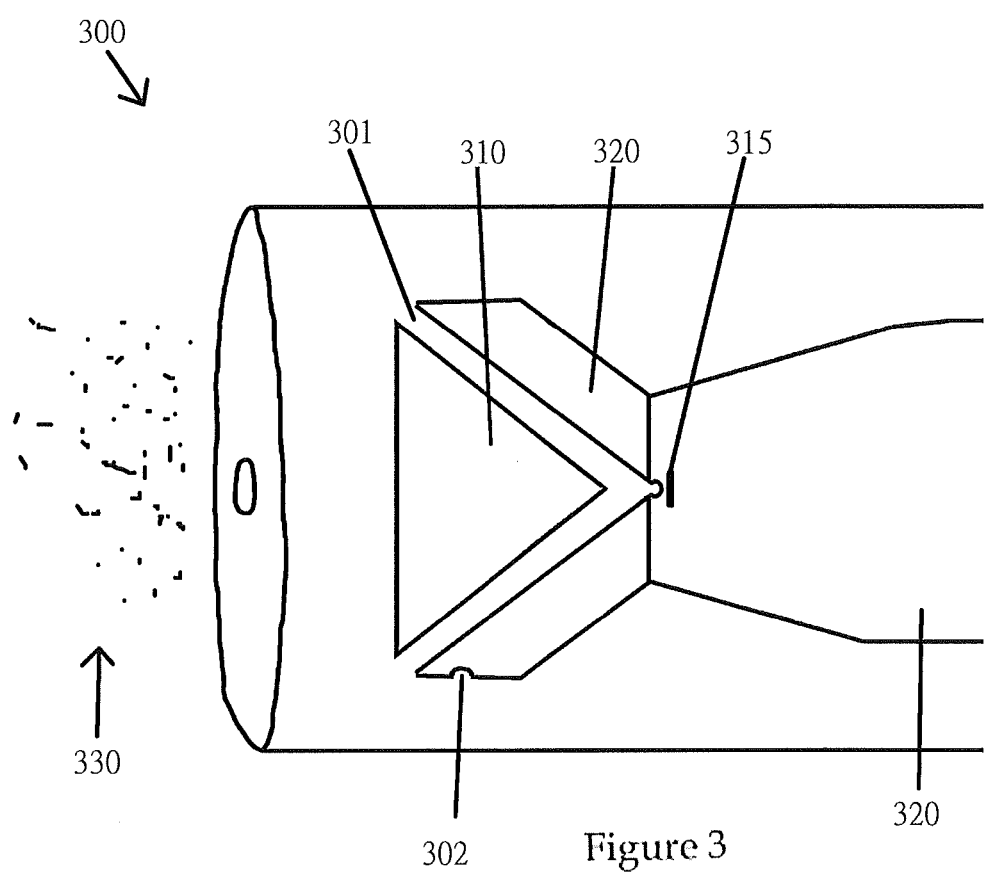
FIG. 3 is a diagram of a possible embodiment of an electronic cigarette which does not include a battery.

FIG. 3 is a diagram of an electronic cigarette 300 which does not include a battery. In an embodiment, the electronic cigarette 300 which does not include a battery may include a device that applies a shearing force on a portion of an e-Liquid, thus reducing its viscosity via the thixotropic effect. In an embodiment a small quantity of e-Liquid (enough for a satisfying e-Smoke generation of a single puff) may be positioned for rotation between two concentric cones 310, 320. Rotation between the two concentric cones 310, 320 may be energized manually, or for example, by the puff energy which can for example rotate a small rotor, or by special grooves (i.e. an airflow groove) 302 in the outer cone's perimeter. The concentric cones 310, 320 may have a small aperture (i.e. an annular gap) 301 at their narrow edge, letting air flowing near the small aperture aerosolize the viscosity-reduced e-Liquid. The rotation between the concentric cones 310, 320 may also warm the e-Liquid, possibly adding to smokers' satisfaction. In an embodiment, the concentric cone 310 is an inner stationary cone and the concentric cone 320 is an outer rotating cone. Other mechanisms may replicate the use of low-viscosity e-Liquid, and aerosolize it via small holes in the e-Liquid container 320. The rotating concentric cones 310, 320 can be referred to as a power source, but may be powered only through air flow. Accordingly, the aerosolization operation does not require a battery or other power source.

In one embodiment, battery-less e-Cigs may include many desirable features. However, in other embodiments, some electronics and possibly some heating of the generated e-Smoke may require a battery or other power source. For example, communication capabilities and control circuitry may require another power source. The e-Cig may include a battery for purposes other than aerosolization which can be smaller, longer-lasting, and with reduced environmental effect. One may consider alternative energy sources, such as solar cells, for this application.

Another energy source, that may supply some heat for a more satisfying smoking experience, while preserving the environment, might be chemical heating. A common method utilized in consumer products such as heating pillows uses sodium acetate, a non-toxic, environmentally-friendly rechargeable heat source that can heat up to 58 degrees centigrade. The e-Liquid can be incorporated into the e-Cig by means of one or several small containers, activated by pressure or other means, to heat the e-Liquid as necessary.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

We claim:
1. An electronic cigarette comprising:
an insulated heating chamber including,
at least one insulating wall, the insulated heating chamber having a volume, the at least one insulating wall being movable so as to change the volume of the insulated heating chamber based on a desired vapor mass to be generated;
a heating element in the insulated heating chamber;
a control chip configured to control heating of the heating element;
an e-Liquid portion in communication with the heating element; and
a controlled valve configured to supply e-Liquid from the e-Liquid portion to the heating element such that the e-Liquid is heated by the heating element to produce a vapor, the controlled valve including a membrane with passageways configured to reduce a droplet size of the e-Liquid.
2. The electronic cigarette of claim 1, wherein the e-Liquid portion includes an e-Liquid container.
3. The electronic cigarette of claim 1, wherein the insulated heating chamber further comprises:
vaporization holes configured to supply the produced vapor therethrough.

* * * * *